United States Patent
Coalter, III et al.

(10) Patent No.: US 7,115,689 B2
(45) Date of Patent: Oct. 3, 2006

(54) SUPPORTED CATALYSTS FOR MANUFACTURE OF POLYMERS

(75) Inventors: Joseph N. Coalter, III, Hurricane, WV (US); Jan W. Van Egmond, Charleston, WV (US); Lewis J. Fouts, Jr., Poca, WV (US); Roger B. Painter, Scott Depot, WV (US); Paul C. Vosejpka, Midland, MI (US)

(73) Assignee: Dow Global Technologies Inc., Midland, MI (US)

(*) Notice: Subject to any disclaimer, the term of this patent is extended or adjusted under 35 U.S.C. 154(b) by 199 days.

(21) Appl. No.: 10/492,139

(22) PCT Filed: Nov. 5, 2002

(86) PCT No.: PCT/US02/35617

§ 371 (c)(1),
(2), (4) Date: Apr. 7, 2004

(87) PCT Pub. No.: WO03/040195

PCT Pub. Date: May 15, 2003

(65) Prior Publication Data

US 2004/0220051 A1 Nov. 4, 2004

Related U.S. Application Data

(60) Provisional application No. 60/338,881, filed on Nov. 6, 2001.

(51) Int. Cl.
*C08F 4/52* (2006.01)
*C08F 4/76* (2006.01)
*B01J 31/38* (2006.01)

(52) U.S. Cl. ............ 526/161; 526/172; 526/351; 526/348; 502/103; 502/152; 502/155

(58) Field of Classification Search ........... 526/172, 526/161
See application file for complete search history.

(56) References Cited

U.S. PATENT DOCUMENTS

| | | | | |
|---|---|---|---|---|
| 5,637,660 A | * | 6/1997 | Nagy et al. | 526/160 |
| 5,783,512 A | | 7/1998 | Jacobsen et al. | 502/124 |
| 6,103,657 A | * | 8/2000 | Murray | 502/155 |
| 6,258,903 B1 | * | 7/2001 | Mawson et al. | 526/113 |
| 6,320,005 B1 | | 11/2001 | Murray | 526/161 |
| 6,566,462 B1 | * | 5/2003 | Murray et al. | 526/114 |
| 6,653,417 B1 | * | 11/2003 | Peterson | 526/172 |
| 2003/0204017 A1 | | 10/2003 | Stevens et al. | 525/53 |

FOREIGN PATENT DOCUMENTS

| WO | WO 01/40330 A1 | * | 6/2001 |
|---|---|---|---|
| WO | WO 02/38628 A2 | | 5/2002 |

\* cited by examiner

*Primary Examiner*—David W. Wu
*Assistant Examiner*—Rip A. Lee

(57) ABSTRACT

A supported catalyst composition and process for preparing high molecular weight polymers of one or more addition polymerizable monomers, especially propylene, said composition comprising: 1) a substrate comprising the reaction product of a solid, particulated, high surface area, metal oxide, metalloid oxide, or a mixture thereof and an organoaluminum compound, 2) a Group 4 metal complex of a polyvalent, Lewis base ligand; and optionally, 3) an activating cocatalyst for the metal complex.

12 Claims, No Drawings

SUPPORTED CATALYSTS FOR MANUFACTURE OF POLYMERS

CROSS REFERENCE STATEMENT

This application claims the benefit of U.S. Provisional Application No. 60/338,881 filed Nov. 6, 2001 and U.S. application Ser. No. 10/139,786 filed May 5, 2002, now U.S. Pat. No. 6,960,635.

BACKGROUND OF THE INVENTION

The present invention relates to supported olefin polymerization catalysts and to a process for preparing polypropylene and other olefin polymers therefrom. The resulting polymers are well known commercially and may be usefully employed in the preparation of solid articles such as moldings, films, sheets and foamed objects by molding, extruding or other processes. The resulting products include components for automobiles, such as bumpers; packaging materials; and other applications.

In U.S. Pat. Nos. 6,320,005 and 6,103,657 certain transition metal amine donor complexes for use as components of olefin polymerization catalysts were disclosed. In WO 02/38628 additional description of such Group 4 metal complexes containing "spectator ligands" such as amino-substituted cyclic amine compounds were disclosed. In the latter publication the use of supports such as silica or alumina for preparing heterogeneous versions of such metal complexes was taught.

SUMMARY OF THE INVENTION

According to the present invention there are now provided a supported, heterogeneous catalyst composition for use in polymerization of addition polymerizable monomers, especially propylene, to form high molecular weight polymers, comprising:

1) a substrate comprising the reaction product of a solid, particulated, high surface area, metal oxide, metalloid oxide, or a mixture thereof and an organoaluminum compound, 2) a Group 4 metal complex of a polyvalent, Lewis base ligand; and optionally, 3) an activating cocatalyst for the metal complex.

In a further embodiment of the present invention there is provided a process for preparing high molecular weight polymers of one or more addition polymerizable monomers, especially propylene or mixtures of ethylene and propylene, comprising contacting one or more addition polymerizable monomers under addition polymerization conditions with a catalyst composition comprising:

1) a substrate comprising the reaction product of a solid, particulated, high surface area, metal oxide, metalloid oxide, or a mixture thereof and an organoaluminum compound, 2) a Group 4 metal complex of a polyvalent, Lewis base ligand; and optionally, 3) an activating cocatalyst for the metal complex.

DETAILED DESCRIPTION OF THE INVENTION

All references to the Periodic Table of the Elements herein shall refer to the Periodic Table of the Elements, published and copyrighted by CRC Press, Inc., 1999. Also, any references to a Group or Groups shall be to the Groups or Groups reflected in this Periodic Table of the Elements using the IUPAC system for numbering groups. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques and general knowledge in the art.

The term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

The term "polymer", includes both homopolymers, that is, polymers prepared from a single reactive compound, and copolymers, meaning polymers prepared by reaction of at least two polymer forming, reactive, monomeric compounds. More specifically, the term "polypropylene" includes homopolymers of propylene and copolymers of propylene and one or more olefins, with the proviso that if the comonomer comprises ethylene, at least 60 percent of the polymer units must be derived from propylene, that is, a methyl-substituted ethylene group. The term "crystalline" if employed, refers to a polymer that exhibits an X-ray diffraction pattern at 25° C. and possesses a first order transition or crystalline melting point (Tm). The term may be used interchangeably with the term "semicrystalline".

Suitable solid, particulated, high surface area, metal oxide, metalloid oxide, or mixtures thereof (interchangeably referred to herein as an inorganic oxide) for use in the preparation of component 1) include: talc, silica, alumina, magnesia, titania, zirconia, $Sn_2O_3$, aluminosilicates, borosilicates, clays, and mixtures thereof. Inorganic oxides suitable for the present invention preferably have a surface area as determined by nitrogen porosimetry using the B.E.T. method from 10 to 1000 $m^2/g$, and preferably from 100 to 600 $m^2/g$. The pore volume of the inorganic oxide as well as the resulting catalyst composition, as determined by nitrogen adsorption, is typically up to 5 $cm^3/g$, advantageously between 0.1 and 3 $cm^3/g$, preferably from 0.2 to 2 $cm^3/g$. The average particle size is chosen to fit the desired application, as explained here-in-after, and typically is from 0.1 to 500 µm, preferably from 1 to 200 µm, more preferably 10 to 100 µm.

Preferred inorganic oxides for use in the present invention include highly porous silicas, aluminas, aluminosilicates, and mixtures thereof. The most preferred support material is silica. The support material may be in granular, agglomerated, pelletized, or any other physical form. Suitable materials include, but are not limited to, silicas available from Grace Davison (division of W.R. Grace & Co.) under the designations SD 3216.30, Davison Syloid ™245, Davison 948 and Davison 952, and from Crossfield Corporation under the designation ES70, and from Degussa AG under the designation Aerosil™812; and aluminas available from Akzo Chemicals Inc. under the designation Ketzen™.

The inorganic oxide is preferably first dehydrated or dried, by heating at temperatures up to 800° C., as is well known in the art, to remove physi-sorbed water, oxygen, carbon dioxide, or other molecules. Alternatively however, in one embodiment the inorganic oxide may initially contain small quantities of water, up to 20 weight percent, which are carefully reacted with a trialkylaluminum compound, especially trimethylaluminum, to prepare alumoxane in situ on the surface of the inorganic oxide. Suitable thermal treatments, if employed, are heating at 100° C. to 1000° C., preferably at 200° C. to 850° C. in an inert atmosphere or under reduced pressure. Typically, this treatment is carried out for 10 minutes to 72 hours, preferably from 0.5 hours to 24 hours.

The solid inorganic oxide is thereafter treated with the organoaluminum compound according to known techniques. Suitable organoaluminum compounds include the well known trihydrocarbyl aluminum compounds, such as trialkylaluminums, especially trimethylaluminum, triethylaluminum, and triisbutylaluminum; trihalohydrocarbyl aluminum compounds, such as tris(pentaflurorphenyl)aluminum; and oxygen containing aluminum compounds, such as alumoxanes.

Suitable alumoxanes for treatment of the inorganic oxide supports herein include polymeric or oligomeric alumoxanes, especially methylalumoxane, and neutral Lewis acid modified polymeric or oligomeric alumoxanes, such as alkylalumoxanes modified by addition of a $C_{1-30}$ hydrocarbyl substituted Group 13 compound, especially a tri(hydrocarbyl)aluminum- or tri(hydrocarbyl)boron compound, or a halogenated (including perhalogenated) derivative thereof, having from 1 to 10 carbons in each hydrocarbyl or halogenated hydrocarbyl group, more especially a trialkylaluminum compound, a perfluorinated tri(aryl)boron compound, or a perfluorinated tri(aryl)aluminum compound. Examples include triisobutyl aluminum- or tri-n-butyl aluminum-modified methylalumoxane, sometimes referred to as modified methalumoxane, or MMAO. The most preferred alumoxane for treatment of the inorganic oxide support is methalumoxane.

The inorganic oxide is treated with the organoaluminum compound by contacting a solution or dispersion thereof with the solid inorganic oxide, optionally at an elevated temperature, in the substantial absence of interfering substances such as oxygen, water or carbon dioxide. The organoaluminum compound is desirably dissolved or dispersed in an inert liquid, such as a hydrocarbon, and the inorganic oxide material immersed, coated, sprayed, or otherwise brought into contact with the solution or dispersion for an appropriate contact period from one minute to several days. The resulting solid may be recovered and devolatilized or rinsed with an inert diluent, especially an aliphatic hydrocarbon to remove excess organoaluminum compound, if desired, prior to use. Typically the quantity of organoaluminum compound used with respect to inorganic oxide is sufficient to provide a concentration of from 0.1 to 50 μmol per g of inorganic oxide, preferably from 1 to 10 μmol/g. The quantity of organoaluminum compound employed is desirably sufficient to saturate the available surface of the support without depositing a significant quantity of material that is capable of being removed by contact with an aliphatic hydrocarbon liquid. Desirably no more than 10 percent, preferably no more than 5 percent, and most preferably no more than 1 percent of the treated support is removed by contacting with hexane at 25° C. for 15 minutes.

Suitable metal complexes of polyvalent Lewis base ligands for use in the present invention include Group 4 metal derivatives, especially hafnium derivatives of hydrocarbylamine substituted heteroaryl compounds of the formula $R^1HN-T-R^2$ (I), said complexes corresponding to the formula:

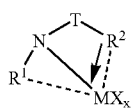

(IA)

wherein:

$R^1$ is selected from alkyl, cycloalkyl, heteroalkyl, cycloheteroalkyl, aryl, and inertly substituted derivatives thereof containing from 1 to 30 atoms not counting hydrogen;

T is a divalent bridging group of from 1 to 20 atoms other than hydrogen, preferably a mono- or di- $C_{1-20}$ hydrocarbyl substituted methylene or silane group, and $R^2$ is a $C_{6-20}$ heteroaryl group containing Lewis base functionality, especially a pyridin-2-yl- or substituted pyridin-2-yl group, and in the metal complex, M is the Group 4 metal, preferably hafnium, X is an anionic, neutral or dianionic ligand group, x is a number from 0 to 5 indicating the number of such X groups, and bonds, optional bonds and electron donative interactions are represented by lines, dotted lines and arrows respectively.

Preferred complexes are those wherein ligand formation results from hydrogen elimination from the amine group and optionally from the loss of one or more additional groups, especially from $R^2$. In addition, electron donation from the Lewis base functionality, preferably an electron pair, provides additional stability to the metal center. Preferred examples of the foregoing polyfunctional Lewis base compounds and the resulting metal complexes correspond to the formulas:

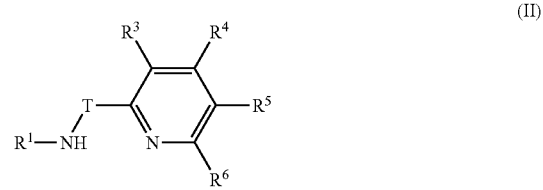

(II)

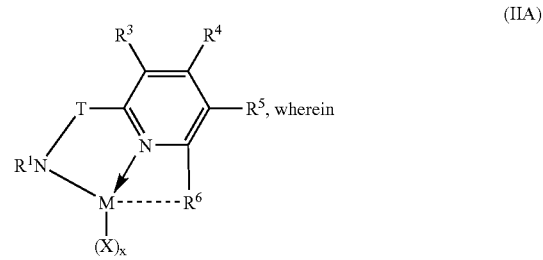

(IIA)

M, X, x, $R^1$ and T are as previously defined, $R^3$, $R^4$, $R^5$ and $R^6$ are hydrogen, halo, or an alkyl, cycloalkyl, heteroalkyl, heterocycloalkyl, aryl, or silyl group of up to 20 atoms not counting hydrogen, or adjacent $R^3$, $R^4$, $R^5$ or $R^6$ groups may be joined together thereby forming fused ring derivatives, and bonds, optional bonds and electron pair donative interactions are represented by lines, dotted lines and arrows respectively.

More preferred examples of the foregoing difunctional Lewis base compounds and metal complexes correspond to the formula:

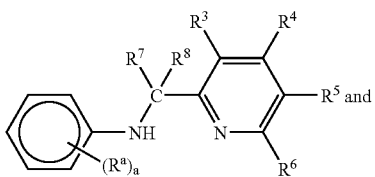

(III)

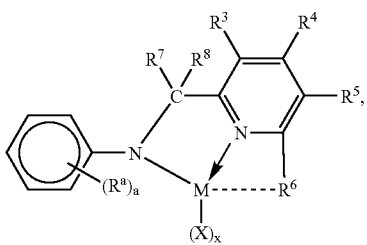

(IIIA)

wherein

M, X, x, $R^1$ and T are as previously defined, $R^3$, $R^4$, $R^5$ and $R^6$ are as previously defined, preferably $R^3$, $R^4$, and $R^5$ are hydrogen, or $C_{1-4}$ alkyl, and $R^6$ is $C_{6-20}$ aryl, most preferably naphthalenyl;

$R^a$ independently each occurrence is $C_{1-4}$ alkyl, and a is 1–5, most preferably $R^a$ in two ortho-positions is isopropyl or t-butyl;

$R^7$ and $R^8$ independently each occurrence are hydrogen, halogen, or a $C_{1-20}$ alkyl or aryl group, most preferably one of $R^7$ and $R^8$ is hydrogen and the other is a $C_{6-20}$ aryl group, especially a fused polycyclic aryl group, most preferably an anthracenyl group, and bonds, optional bonds and electron pair donative interactions are represented by lines, dotted lines and arrows respectively.

Highly preferred polyfunctional Lewis base compounds and metal complexes for use herein correspond to the formula:

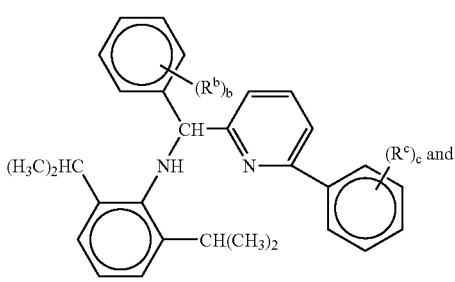

(IV)

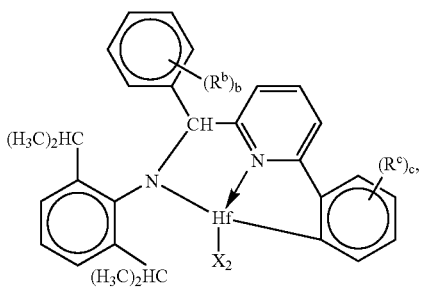

(IVA)

wherein X each occurrence is halide, N,N-dimethylamido, or $C_{1-4}$ alkyl, and preferably each occurrence X is methyl;

$R^b$ independently each occurrence is hydrogen, halogen, $C_{1-20}$ alkyl, or $C_{6-20}$ aryl, or two adjacent $R^b$ groups are joined together thereby forming a ring, and b is 1–5; and $R^c$ independently each occurrence is hydrogen, halogen, $C_{1-20}$ alkyl, or $C_{6-20}$ aryl, or two adjacent $R^c$ groups are joined together thereby forming a ring, and c is 1–5.

Most highly preferred examples of metal complexes for use according to the present invention are complexes of the following formulas:

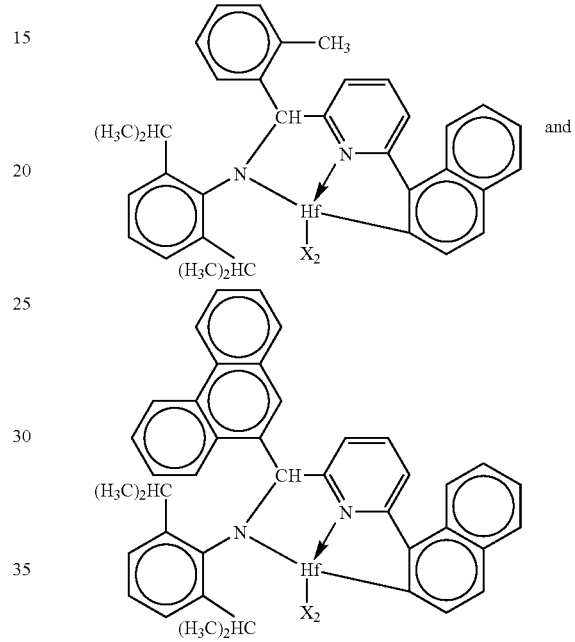

wherein X each occurrence is halide, N,N-dimethylamido, or $C_{1-4}$ alkyl, and preferably each occurrence X is methyl.

Examples of metal complexes usefully employed according to the present invention include:

[N-(2,6-di(1-methylethyl)phenyl)amido)(o-tolyl)(α-naphthalen-2-diyl(6-pyridin-2-diyl)methane)]hafnium dimethyl;

[N-(2,6-di(1-methylethyl)phenyl)amido)(o-tolyl)(α-naphthalen-2-diyl(6-pyridin-2-diyl)methane)]hafnium di(N,N-dimethylamido);

[N-(2,6-di(1-methylethyl)phenyl)amido)(o-tolyl)(α-naphthalen-2-diyl(6-pyridin-2-diyl)methane)]hafnium dichloride;

[N-(2,6-di(1-methylethyl)phenyl)amido)(phenanthren-5-yl)(α-naphthalen-2-diyl(6-pyridin-2-diyl)methane)]hafnium dimethyl;

[N-(2,6-di(1-methylethyl)phenyl)amido)((phenanthren-5-yl)(α-naphthalen-2-diyl(6-pyridin-2-diyl)methane)] hafnium di(N,N-dimethylamido); and

[N-(2,6-di(1-methylethyl)phenyl)amido)(phenanthren-5-yl)(α-naphthalen-2-diyl(6-pyridin-2-diyl)methane)]hafnium dichloride.

Under the reaction conditions used to prepare the metal complexes used in the present invention, it has been discovered that the hydrogen of the 2-position of the (α-naphthalene group substituted at the 6-position of the pyridin-2-yl group is subject to elimination, thereby uniquely forming metal complexes wherein the metal is covalently bonded to both the resulting amide group and to the 2-position of the α-naphthalenyl group, as well as stabilized by coordination to the pyridinyl nitrogen atom through the electron pair of the nitrogen atom.

The foregoing metal complexes are conveniently prepared by standard metallation and ligand exchange procedures involving a source of the Group 4 metal and the neutral polyfunctional ligand source. The complexes may also be prepared by means of an amide elimination and hydrocarbylation process starting from the corresponding Group 4 metal tetraamide and a hydrocarbylating agent, such as trimethylaluminum, as disclosed in WO 02/38628. Other techniques may be used as well.

The Group 4 metal complexes may be activated to form the actual catalyst composition by combination with a cocatalyst, preferably an aluminoxane, a cation forming cocatalyst, or a combination thereof. Preferably, the sole activating cocatalyst is an alumoxane which is a portion of the alumoxane used to treat the surface of the metal- or metalloid-oxide support, or generated in situ, on the surface of the support by reaction of an aluminum trialkyl compound, especially trimethylaluminum, with water present on the surface of the metal oxide. In this event, additional activating cocatalyst is not required to be separately combined with the metal complex before supporting the metal complex, and for this reason component 3) is stated as being optionally added to the composition.

Suitable alumoxanes for activation of the metal complexes herein include the same compounds used for treatment of the inorganic oxide supports, namely polymeric or oligomeric alumoxanes, especially methylalumoxane, and neutral Lewis acid modified polymeric or oligomeric alumoxanes, such as alkylalumoxanes modified by addition of a $C_{1-30}$ hydrocarbyl substituted Group 13 compound, especially a tri(hydrocarbyl)aluminum- or tri(hydrocarbyl)boron compound, or a halogenated (including perhalogenated) derivative thereof, having from 1 to 10 carbons in each hydrocarbyl or halogenated hydrocarbyl group, more especially a trialkylaluminum compound, a perfluorinated tri(aryl)boron compound, or a perfluorinated tri(aryl)aluminum compound. Examples include triisobutyl aluminum- or tri-n-butyl aluminum-modified methylalumoxane, sometimes referred to as modified methalumoxane, or MMAO.

The Group 4 metal complexes may also be rendered catalytically active by combination with a cation forming cocatalyst, such as those previously known in the art for use with Group 4 metal olefin polymerization complexes. Suitable cation forming cocatalysts for use herein include neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluoro-phenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium-, lead- or silver salts of compatible, noncoordinating anions; and combinations of the foregoing cation forming cocatalysts and techniques. The foregoing activating cocatalysts and activating techniques have been previously taught with respect to different metal complexes for olefin polymerizations in the following references: EP-A-277,003, U.S. Pat. Nos. 5,153,157, 5,064,802, 5,321,106, 5,721,185, 5,350,723, 5,425,872, 5,625,087, 5,883,204, 5,919,983, 5,783,512, WO 99/15534, and WO99/42467.

It should be noted that the foregoing activating cocatalysts other than an alumoxane, are not preferably included in the invented composition, in as much as the best results have generally been obtained by the use of inorganic oxide supports that have been treated with methalumoxane, and optionally, additional methalumoxane cocatalyst.

During the polymerization, a mixture of monomers is contacted with the supported, activated catalyst composition according to any suitable polymerization conditions. The process is characterized by use of elevated temperatures and pressures. Hydrogen may be employed as a chain transfer agent for molecular weight control according to known techniques if desired. As in other similar polymerizations, it is highly desirable that the monomers and solvents employed be of sufficiently high purity that catalyst deactivation does not occur. Any suitable technique for monomer purification such as devolatilization at reduced pressures, contacting with molecular sieves or high surface area alumina, or a combination of the foregoing processes may be employed.

In a preferred embodiment of the invention the supported catalysts are employed in either a solution, slurry or gas phase polymerization. It has been discovered that if a minor proportion of ethylene is present or is first present in a polymerization of propylene using the catalysts of the present invention, polymers having very high molecular weights can be prepared. Moreover, the process for preparing such interpolymers is more efficient, compared to processes in which ethylene is completely absent. The quantity of ethylene added to the reactor is a minor amount compared to the quantity of propylene, and may be extremely small, preferably greater than 0.001 mole percent, based on total monomer content, more preferably from 0.01 to 10 mole percent. Desirably the resulting copolymer possesses in polymerized form from 0.1 to 25 mole percent ethylene. Further desirably such copolymers also possess a molecular weight distribution, Mw/Mn, greater than 4.0, preferably greater than 5.0. Additionally the polymers desirably possess very rapid crystallization rates, as evidenced by an isothermal crystallization half time (ICHT) of less than about 1 minute at 120° C. Additionally, they are characterized by unique $^{13}C$ NMR spectrum, showing peaks corresponding to such regio-error at about 14.6 and about 15.7 ppm, with the peaks being of equal or approximately equal intensity (that is, the integrated areas of the two peaks differ by less than 10 percent).

The polymerization is desirably carried out as a continuous polymerization, in which catalyst components, monomers, and optionally solvent, adjuvants, scavengers, and polymerization aids are continuously supplied to the reaction zone and polymer product continuously removed therefrom. Within the scope of the terms "continuous" and "continuously" as used in this context are those processes in which there are intermittent additions of reactants and removal of products at small regular intervals, so that, over time, the overall process is continuous.

The catalyst compositions can be advantageously employed in a high pressure, solution, slurry, or gas phase polymerization process. For a solution polymerization process it is desirable to employ homogeneous dispersions of the catalyst components in liquid diluent in which the polymer is soluble under the polymerization conditions employed. One such process utilizing an extremely fine silica or similar dispersing agent to produce such a homogeneous catalyst dispersion is disclosed in U.S. Pat. No. 5,783,512. A high pressure process is usually carried out at temperatures from 100° C. to 400° C. and at pressures above 500 bar (50 MPa). A slurry process typically uses an inert hydrocarbon diluent and temperatures of from 0° C. up to a temperature just below the temperature at which the resulting polymer becomes substantially soluble in the inert polymerization medium. Preferred temperatures in a slurry polymerization are from 30° C., preferably from 60° C. up to 115° C., preferably up to 100° C. Pressures typically range from atmospheric (100 kPa) to 500 psi (3.4 MPa).

Preferably for use in gas phase polymerization processes, the support material and resulting catalyst has a median particle diameter from 20 to 200 µm, more preferably from 30 µm to 150 µm and most preferably from 50 µm to 100 µm. Preferably for use in slurry polymerization processes, the support has a median particle diameter from 1 µm to 200 µm, more preferably from 5 µm to 100 µm, and most preferably from 10 µm to 80 µm. Preferably for use in solution or high pressure polymerization processes, the support has a median particle diameter from 0.1 µm to 40 µm, more preferably from 1 µm to 30 µm, and most preferably from 2 µm to 20 µm.

The supported catalyst composition of the present invention can also be employed to advantage in a gas phase polymerization process. Such processes are used commercially on a large scale for the manufacture of polypropylene, ethylene/propylene copolymers, and other olefin polymerizaitons. The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported or suspended above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect, often referred to as operation in the condensing mode. The volatile liquid employed in this case can be, for example, a volatile inert liquid, for example, a saturated hydrocarbon having 3 to 8, preferably 4 to 6, carbon atoms. In the case that the monomer or comonomer itself is a volatile liquid, or can be condensed to provide such a liquid, this can suitably be fed to the bed to provide an evaporative cooling effect. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream. This type of process is described, for example in EP-89691; U.S. Pat. No. 4,543,399; WO-94/25495 and U.S. Pat. No. 5,352,749. A particularly preferred method of recycling the liquid to the bed is to separate the liquid from the recycle gas stream and to reinject this liquid directly into the bed, preferably using a method which generates fine droplets of the liquid within the bed. This type of process is described in WO-94/28032.

The polymerization reaction occurring in the gas fluidized bed is catalyzed by the continuous or semi-continuous addition of catalyst composition. The catalyst composition may be subjected to a prepolymerization step, for example, by polymerizing a small quantity of olefin monomer in a liquid inert diluent, to provide a catalyst composite comprising supported catalyst particles embedded in olefin polymer particles if desired as well.

The polymer is produced directly in the fluidized bed by polymerization of the monomer or mixture of monomers on the fluidized particles of catalyst composition, supported catalyst composition or prepolymerized catalyst composition within the bed. Start-up of the polymerization reaction is achieved using a bed of preformed polymer particles, which are preferably similar to the desired polymer, and conditioning the bed by drying with inert gas or nitrogen prior to introducing the catalyst composition, the monomers and any other gases which it is desired to have in the recycle gas stream, such as a diluent gas, hydrogen chain transfer agent, or an inert condensable gas when operating in gas phase condensing mode. The produced polymer is discharged continuously or semi-continuously from the fluidized bed as desired.

The gas phase processes most suitable for the practice of this invention are continuous processes which provide for the continuous supply of reactants to the reaction zone of the reactor and the removal of products from the reaction zone of the reactor, thereby providing a steady-state environment on the macro scale in the reaction zone of the reactor. Products are readily recovered by exposure to reduced pressure and optionally elevated temperatures (devolatilization) according to known techniques. Typically, the fluidized bed of the gas phase process is operated at temperatures greater than 50° C., preferably from 60° C. to 110° C., more preferably from 70° C. to 110° C.

Suitable gas phase processes which are adaptable for use in the process of this invention are disclosed in U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; 5,556,238; 5,541,270; 5,608,019; and 5,616,661.

The skilled artisan will appreciate that the invention disclosed herein may be practiced in the absence of any component which has not been specifically disclosed.

The following examples are provided as further illustration of the invention and are not to be construed as limiting. Unless stated to the contrary all parts and percentages are expressed on a weight basis. The term "overnight", if used, refers to a time of approximately 16–18 hours, the term "room temperature", refers to a temperature of 20–25° C., and the term "mixed alkanes" refers to a commercially obtained mixture of $C_{6-9}$ aliphatic hydrocarbons available under the trade designation Isopar E®, from Exxon Chemicals Inc. In the event the name of a compound herein does not conform to the structural representation thereof, the structural representation shall control. The synthesis of all metal complexes and the preparation of all screening experiments were carried out in a dry nitrogen atmosphere using dry box techniques. All solvents used were HPLC grade and were dried before their use.

EXAMPLES 1–6 AND COMPARATIVES 1 AND 2

Component 1) Preparation

1A) Davison 948™ silica (949 g, available from Grace Davison Company) which had been heated at 600° C. for 3 hours under a nitrogen purge was added to toluene (2400 g) containing methylalumoxane (MAO, Akzo Nobel, Inc. 1314 mL of a 13.7 percent toluene solution). The mixture was stirred for 30 minutes, and the temperature of the mixture was increased to 70° C. and the volatiles were removed in vacuo. The resulting dry powder was heated an additional 1 hour under vacuum. The resulting alumoxane modified silica, was a free flowing solid having an aluminum content of 4.5 mmol/g. Contacting with hexane at 25° C. resulted in less than 1 percent weight loss.

1B) Davison 948™ silica (370 g) which had been heated at 500° C. for 3 hours under a nitrogen purge was slurried in enough isopentane to obtain a easily stirred mixture. 549 ml of a 12.9 percent (4.14 M Al) toluene solution of a tri(n-octyl)aluminum modified methylalumoxane (MMAO-12, Akzo-Noble, Inc.) was added at room temperature. The mixture was stirred for 1 hour, the supernatant was removed via cannula, and the treated silica was washed with isopentane (1000 ml) and dried under high vacuum. The resulting free flowing, powder had an aluminum content of 4.5 mmol/g. Contacting with hexane at 25° C. resulted in less than 1 percent weight loss.

1C) Davison 948™ silica (6.00 g) which had been heated at 500° C. for 3 hours under a nitrogen purge was slurried in hexane (24 g) and then treated with 8.00 ml of a 21 percent triethylaluminum/hexane solution at room temperature. The mixture was stirred for 30 minutes, collected on a filter, and the treated silica was washed with hexane (2×10 ml) and dried under high vacuum. The resulting free flowing, powder had an aluminum content of approximately 1.1 mmol/g. Contacting with hexane at 25° C. resulted in less than 1 percent weight loss.

1D) Davison 948™ silica (6.00 g) was heated at 500° C. for 3 hours under a nitrogen purge prior to use.

Component 2) Preparation

2A) To a flask containing toluene and (2,6-di(1-methylethyl)phenylamino)(o-tolyl)((α-naphthalenyl(6-pyridin-2-diyl))methane, one equivalent of n-butyllithium is added. After deprotonation is complete, one equivalent of hafnium tetrachloride is added and the mixture is heated to reflux for at least 1 hour. After cooling, a minimum of 3 equivalents of methyl magnesium bromide is added. After methylation is complete, the crude product is separated from the inorganic salts by filtration, washed with hexane, and isolated by removal of the volatiles in vacuo.

2B) [N-(2,6-di(1-methylethyl)phenylamido)(o-tolyl)((α-naphthalen-2-diyl(6-pyridin-2-diyl))methane)]hafnium dichloride, is obtained by treatment of a toluene solution of 2A with 2 equivalents of anhydrous triethylammonium chloride. After protonolysis is complete, the product is filtered to remove insolubles, isolated by removing volatiles in vacuo, and washing the product with hexane before final drying in vacuo.

Component 3) Preparation

3A) In a glass ampoule, 16.5 µL of a 19.6 percent toluene solution of triethylaluminum were combined with 260 mg of a 10.4 percent toluene solution of the methylbis-($C_{18-22}$alkyl)ammonium salt of p-hydroxyphenyltris(pentafluorophenyl)borate: [(p-HOC$_6$H$_4$)B(C$_6$F$_5$)$_3$][NHMe(C$_{18-22}$H$_{37-45}$)$_2$](0.024 µmol) and stirred for 15 minutes. Prior to use the product was diluted with 400 mg toluene.

3B) Methylbis($C_{18-22}$ alkyl)ammonium tetrakis(pentafluorophenyl)borate: [NHMe(C$^{18-22}$H$_{37-45}$)$_2$]$^+$[B(C$_6$F$_5$)$_4$]$^{31}$ was prepared according to U.S. Pat. No. 5,919,983.

Supported Catalyst Preparation

Example 1 (No separately added cocatalyst) In a glass flask containing 40 mL hexane, 10.13 g of the treated support 1A (45.6 mmol Al) was added and stirred to form a slurry. Component 2A (70.0 mg, 0.101 mmol Hf) was added and the resulting mixture stirred for 3 hours. The solids were allowed to settle, the supernatant was removed by decantation, and the solids were dried under high vacuum, leaving the catalyst composition as a free flowing powder, in quantitative yield. Hf content=10 µmol Hf/g. Al/Hf (molar ratio) =450:1.

Example 2 (No separately added cocatalyst; supported catalyst generated in situ and used without isolation) In a vial, 0.2 mL of a 0.005 M hexane solution of component 2A was added to a slurry of 0.26 g of support 1A in 2 mL of hexane. After stirring for 1 h, the mixture was injected directly into the polymerization vessel. Hf content=3.85 µmol/g. Al/Hf (molar ratio)=1170:1

Example 3 (No separately added cocatalyst; supported catalyst generated in situ and used without isolation) In a vial, 0.2 mL of a 0.005 M hexane solution of component 2A was added to a slurry of 0.222 g of support 1B in 2 mL of hexane. After stirring for 60 minutes, the mixture was injected directly into the polymerization vessel. Hf content=4.50 µmol/g. Al/Hf (molar ratio)=1000:1

Example 4 (with ammonium borate cocatalyst 3A) To 1.00 g of the triethylaluminum treated support component 1C (1.1 mmol Al) in a flask, component 3A (680 mg) was added dropwise with stirring. Additional toluene (200 mg) was added and stirring continued for 1 h. Component 2A (13.8 mg, 20 µmol Hf) in 500 mg toluene was added and the resulting mixture stirred for one hour. Hexane (25 ml) was added and stirring continued for 2 h. The solids were collected by filtration, washed with 20 mL hexane and dried, leaving the catalyst composition as a free flowing powder, in quantitative yield. Hf content=20 µmol Hf/g. Al/Hf (molar ratio)=55:1. B:Hf (molar ratio)=1.2:1.

Example 5 (with ammonium borate cocatalyst 3B) To a mixture of 1.00 g of the triethylaluminum treated support component 1C (1.1 mmol Al) and 4.0 mL of hexane in a flask, a mixture of 2.50 g of a 1.06 percent methylcyclohexane solution of component 3B and 13.9 mg of component 2A which was premixed for 30 minutes, was added dropwise with stirring. The combined mixtures were stirred for 30 minutes and the volatiles were removed in vacuo, leaving the catalyst composition as a free flowing powder, in quantitative yield. Hf content=20 µmol Hf/g. Al/Hf (molar ratio)=55:1. B:Hf (molar ratio)=1.1:1.

Example 6 (No separately added cocatalyst) In a glass vial containing 4.0 mL hexane, 0.44 g of the treated support 1A was added and stirred to form a slurry. Component 2B (0.4 mL of a 0.005 M toluene solution) was added and the mixture stirred for 1 h. The resulting mixture was injected directly into the reactor without isolation of the supported catalyst. Hf content=4.5 µmol Hf/g. Al/Hf (molar ratio)=1000:1.

Comparative 1 (Untreated silica, not an example of the invention) In a glass flask containing 5 mL hexane, 1.00 g of Davison 948™ silica which had been heated at 500° C. for 3 hours under a nitrogen purge, was added and stirred to form a slurry. A premixed hexane solution of Component 2A (4.15 mg, 6.0 mmol Hf, 1.0 mL hexane) and the MMAO-12 methalumoxane cocatalyst as a 12.9 percent aluminum/toluene solution (1.09 mL, 4500 μmol Al, Akzo-Noble) was added and the resulting mixture stirred overnight. The volatiles were removed under high vacuum leaving the catalyst composition as a free flowing powder, in quantitative yield. Hf content=3.53 μmol Hf/g. Al:Hf (molar ratio)=750:1.

Comparative 2 (Untreated silica, not an example of the invention) In a glass flask containing 5 mL hexane, 1.00 g of Davison 948™ silica which had been heated at 500° C. for 3 hours under a nitrogen purge, was added and stirred to form a slurry. A premixed toluene solution of Component 2A (4.15 mg, 6.0 mmol Hf, 1.0 mL toluene) and methalumoxane cocatalyst as a 13.7 percent aluminum/toluene solution (0.96 mL, 4500 μmol Al, MAO-3, Albemarle) was added and the resulting mixture stirred overnight. The volatiles were removed under high vacuum leaving the catalyst composition as a free flowing powder, in quantitative yield. Hf content=4.72 μmol Hf/g. Al:Hf (molar ratio)=750:1.

Polymerization

A 1 liter stirred, jacketed, polymerization reactor was charged with 400 g propylene and heated to 60° C., resulting in an internal pressure of 375 psi (2.8 MPa). Triisobutylaluminum (0.4 g, 2 mmol) in 10 ml hexane solvent was added to the reactor contents and circulated for 10 minutes to scavenge impurities. Next, the desired quantity of catalyst slurry followed by an additional 10 ml hexane to purge the line was added via a transfer line. The reaction temperature was maintained at 60° C. After 30 minutes polymerization time, the reactor was vented and cooled and the resulting polymer removed from the reactor. Results are contained in Table 1.

Polymer Characterization

The following analytical studies were performed on the polymers prepared according to the invention. Results are reported for the polymer of Run 3 in Tables 2 and 3.

GPC, xylene solubles (XS), and NMR measurements were performed according to standard procedures.

Morphology (polymer particle integrity and lack of lumping or friability) was determined qualitatively by observation.

Melt flow rate (MFR) (g/10 minutes) was determined in accordance with ASTM D-1238 condition L.

Differential Scanning Calorimetry (DSC) heat-cool-heat experiments were performed using a Perkin-Elmer DSC7 instrument. The first heating was done at 10° C./minute, then cooling at 10° C./min to crystallize the polymer, then second heating was done at 10° C./minute.

Percent crystallinity was determined from DSC data using the equation:

$$Xc = 100 \; \Delta Hf/\Delta Hfo$$

where ΔHf is the measured heat of fusion of the sample, and ΔHfo is the heat of fusion of 100 percent crystalline polymer, namely 39.4 calories/gm.

For measuring ICHT (isothermal crystallization half time) by differential scanning calorimeter (Perkin Elmer DSC7) the following procedure was used. The polymer was melted at 250° C. (for 3 minutes), then cooled rapidly (200° C./minute) to 120° C. (crystallization temperature), then held isothermally in time mode at 120° C. until it crystallized. The time to the peak of the crystallization exotherm was taken as the ICHT. Lower ICHT indicates faster crystallization rate.

TABLE 2

General Characteristics - Run 3

| Mn | Mw | Mz | Mw/Mn | Morphology | MFR | XS (percent) |
|---|---|---|---|---|---|---|
| 249,500 | 1,275,000 | 3,825,000 | 5.11 | Good to excellent | 0.04 | 0.64 |

TABLE 1

| run | Catalyst | Complex | Support | Activator** | Efficiency (kg/g Hf) |
|---|---|---|---|---|---|
| 1 | Ex. 1 | 2A | 1A | — | 254 |
| 2 | Ex. 2 | " | 1A | — | 969 |
| 3 | Ex. 3 | " | 1B | — | 214 |
| 4 | Ex. 4 | " | 1C | 3A | 117 |
| 5 | Ex. 5 | " | 1C | 3B | 171 |
| 6 | Ex. 6 | 2B | 1A | — | 168 |
| 7* | Comp. 1 | 2A | 1D | MMAO-12 | 62 |
| 8* | Comp. 2 | " | 1D | MAO | 2 |

*comparative not an example of the invention, support not pretreated with organoaluminum compound prior to contacting with metal complex
**activator combined with metal complex prior to contact with support As may be seen by reference to the results contained in table 1, the use of silica that has been modified by treatment with an aluminum compound, especially an alumoxane, gives the best results, particularly when used immediately following preparation without isolation of the supported solid catalyst; and use of unmodified silica support, even in combination with use of an alumoxane cocatalyst gave extremely poor results.

TABLE 3

Melting and crystallization data - Run 3

| Tm, ° C. | Tc, ° C. | Heat of fusion (J/gm) | Percent Crystallinity | ICHT 120° C. (min) |
|---|---|---|---|---|
| 146 | 112 | 89.6 | 54.1 | <1 |

As can be seen from the Tables, the polypropylene resin from run 3 has a broad molecular weight distribution (MWD) and a rapid crystallization rate. The broad MWD is a particularly surprising feature of this polypropylene and is believed to result from the interaction of the active catalyst components of the invention. While only homopolymer polypropylenes were made, it is believed that propylene/ethylene copolymers made with the present supported catalyst composition will exhibit a similar broad MWD.

The polypropylene of runs 1 through 4 also had regio-errors as determined by $^{13}$C NMR spectroscopy. In particular, the regio-error frequency was 8 to 14 per 1000 propylene units. The regio-error shows up as a twin peaks at about 14.6 and about 15.7 ppm in the $^{13}$C NMR spectrum, with the peaks having about equal intensity. Polypropylene homopolymers made from the active catalyst of the invention typically have at least 50 percent more of this regio-error than a comparable polypropylene homopolymer prepared with a Ziegler-Natta catalyst. Propylene/ethylene copolymers made with the present catalyst composition also are characterized by $^{13}C$ NMR spectra exhibiting a similar regio-error.

Isothermal crystallization half time (ICHT) at 120° C. for the polypropylene resins made in runs 1–4 were surprisingly fast (1 min or less). This indicates the polymers possess a crystallization rate faster than commercially available polypropylenes made using zirconium based metallocene catalysts.

The invention claimed is:

1. A supported, heterogeneous catalyst composition for use in polymerization of addition polymerizable monomers, comprising:
   1) a substrate comprising the reaction product of a solid, particulated, high surface area, metal oxide, metalloid oxide, or a mixture thereof and an organoaluminum compound,
   2) a Group 4 metal complex of a polyvalent, Lewis base ligand selected from the group consisting of:

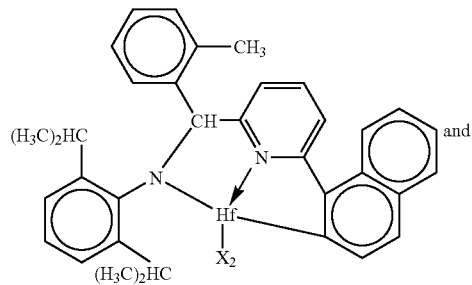

and

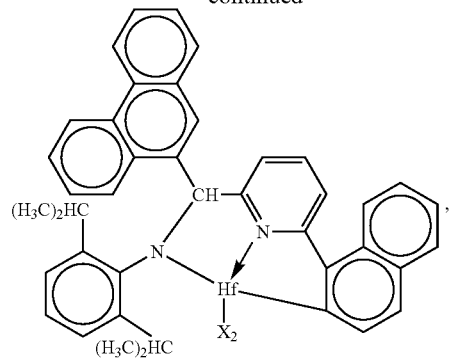

wherein X each occurrence is halide, N,N-dimethylamido, or $C_{1-4}$ alkyl; and optionally,
   3) an activating cocatalyst for the metal complex.

2. A process for preparing high molecular weight polymers of one or more addition polymerizable monomers comprising contacting said one or more addition polymerizable monomers under addition polymerization conditions with a catalyst composition according to claim 1.

3. A process according to claim 2 wherein propylene is homopolymerized.

4. A process according to claim 2, wherein propylene and ethylene in an amount from 0.001 to 10 percent of the total monomer weight are copolymerized.

5. A polypropylene made by the process of claim 3.

6. A polypropylene of claim 5, having a molecular weight distribution of at least 4.

7. A polypropylene of claim 5, having a molecular weight distribution of at least 5.

8. A polypropylene of claim 6, exhibiting an isothermal crystallization half time of less than 1 minute at 120° C.

9. A propylene copolymer made by the process of claim 4.

10. The copolymer of claim 9, having a molecular weight distribution of at least 4.

11. The copolymer of claim 9, having a molecular weight distribution of at least 5.

12. The copolymer of claim 9, characterized by a $^{13}C$ NMR spectrum containing peaks corresponding to a regio-error at about 14.6 and about 15.7 ppm, wherein the peaks are of about equal intensity.

* * * * *